(12) United States Patent
Bayram et al.

(10) Patent No.: US 10,151,709 B2
(45) Date of Patent: Dec. 11, 2018

(54) DEVICE AND METHOD FOR EVALUATION OF A MATERIAL

(71) Applicant: PaneraTech, Inc., Chantilly, VA (US)

(72) Inventors: Yakup Bayram, Falls Church, VA (US); Alexander Ruege, Fairfax, VA (US); Eric Walton, Columbus, OH (US); Peter Hagan, Alexandria, VA (US)

(73) Assignee: PaneraTech, Inc., Chantilly, VA (US)

( * ) Notice: Subject to any disclaimer, the term of this patent is extended or adjusted under 35 U.S.C. 154(b) by 0 days.

(21) Appl. No.: 14/732,831

(22) Filed: Jun. 8, 2015

(65) Prior Publication Data

US 2015/0362439 A1 Dec. 17, 2015

Related U.S. Application Data

(60) Provisional application No. 62/010,654, filed on Jun. 11, 2014, provisional application No. 62/073,193, filed on Oct. 31, 2014.

(51) Int. Cl.
*G01N 22/02* (2006.01)
*G01M 3/16* (2006.01)
*G01M 3/40* (2006.01)

(52) U.S. Cl.
CPC .............. *G01N 22/02* (2013.01); *G01M 3/16* (2013.01); *G01M 3/40* (2013.01)

(58) Field of Classification Search
CPC ..................................................... G01N 22/02
See application file for complete search history.

(56) References Cited

U.S. PATENT DOCUMENTS

| 6,198,293 | B1 | 3/2001 | Woskov et al. |
| 9,488,601 | B2 | 11/2016 | Ruege et al. |
| 2005/0200549 | A1* | 9/2005 | Thompson ............... H01Q 9/28 |
| | | | 343/795 |

(Continued)

OTHER PUBLICATIONS

Tuncay, O. "Wireless Strain Gauge System In a Multipath Environment." A Thesis Presented in Partial Fulfillment of the Requirements for the Degree Master of Science in the Graduate School of the Ohio State University. 2008.

(Continued)

*Primary Examiner* — Noam Reisner
(74) *Attorney, Agent, or Firm* — Whiteford, Taylor & Preston, LLP; Gregory M. Stone

(57) ABSTRACT

Disclosed is an improved device and method to evaluate the status of a material by scanning an area that overlaps a region of the material under evaluation. The device and method are operative to identify a leakage of a first material into a second material, such as a molten material surrounded by a refractory material, to measure the thickness of the second material, using electromagnetic waves, and to generate images. The device is designed to reduce a plurality of reflections associated with the propagation of electromagnetic waves launched into the material under evaluation, by a sufficient extent so as to enable detection of electromagnetic waves of interest reflected from remote discontinuities present in between the device and the enclosed material. Furthermore, the device can be configured to scan areas of interest in either a portable or fixed configuration, manually in a standalone mode or as part of an automated system.

30 Claims, 10 Drawing Sheets

(56) References Cited

U.S. PATENT DOCUMENTS

| | | | |
|---|---|---|---|
| 2008/0303710 A1* | 12/2008 | Kienzle | G01F 23/284 |
| | | | 342/124 |
| 2010/0033391 A1* | 2/2010 | McLean | H01Q 13/0275 |
| | | | 343/786 |
| 2011/0085636 A1* | 4/2011 | Dennerlein | A61B 6/032 |
| | | | 378/4 |
| 2012/0192617 A1 | 8/2012 | Walton et al. | |
| 2013/0144554 A1* | 6/2013 | Walton | G01B 15/02 |
| | | | 702/172 |
| 2013/0268237 A1 | 10/2013 | Wolfe et al. | |
| 2015/0276577 A1* | 10/2015 | Ruege | G01B 15/02 |
| | | | 324/71.2 |

OTHER PUBLICATIONS

International Search Report issued in corresponding International Patent Application No. PCT/US15/34620 dated Sep. 15, 2015.

* cited by examiner

DEVICE AND METHOD FOR EVALUATION OF A MATERIAL

CROSS REFERENCE TO RELATED APPLICATION

This application is based upon co-pending U.S. Provisional Patent Application Ser. No. 62/010,654 entitled "Imaging System and Method for Evaluation of a Material," filed with the U.S. Patent and Trademark Office on Jun. 11, 2014, and upon co-pending U.S. Provisional Patent Application Ser. No. 62/073,193 entitled "Scanning Device and Method for Evaluation of a Material," filed with the U.S. Patent and Trademark Office on Oct. 31, 2014, by the inventors herein, the specifications of which are incorporated herein by reference.

FIELD OF THE INVENTION

The present invention relates to devices and methods for evaluating the status of a material. More particularly, the present invention relates to devices and methods for determining a property of a material, including the presence of a first material within a second material, using electromagnetic waves.

BACKGROUND OF THE INVENTION

A number of evaluation devices and methods exist within various industries for measuring properties during and after formation of certain materials. The penetration or leakage of an enclosed first material into a second enclosing material is critically important in a number of industries and may require frequent evaluation due to the compromised integrity of the second material in terms of structural flaws and wear. In particular, the wall thickness of glass and plastic containers using non-contact reflective and/or absorptive techniques by deploying sensors and emitters to direct radiation towards the container have been addressed in the prior art, as described in U.S. Pat. App. Publication No. 2013/0268237 by Wolfe et al. However, the devices used are primarily directed to evaluating the thickness of manufactured glass and plastic containers by means of using radiation capable of passing through those materials without sustaining significant losses in the levels of such radiation or accessing more than just one external surface of such materials.

On a larger scale, some industries such as the glass, steel, and plastic industries use large furnaces to melt the raw material used for processing. These furnaces may reach a length equivalent to the height of a 20-story building. Thus, they are a key asset for manufacturers in terms of costs and operational functionality. In order to minimize the internal heat loss at high operating temperatures, these furnaces are constructed using refractory material, having very high melting temperatures and good insulation properties, to create a refractory melting chamber. However, the inner walls of the refractory chamber of the furnace will degrade during operation. The effects of this degradation include inner surface erosion, stress cracks, and refractory material diffusion into the molten material.

More importantly, the leakage of molten material into the enclosing layers of refractory material may have serious consequences to the furnace operators. Currently, there is no well-established device for deterministically measuring the level of penetration of molten material into the walls of such furnaces. As a result, manufacturers experience either an unexpected leakage of molten material through the furnace wall or conservatively shut down the furnace for re-build to reduce the likelihood of any potential leakage, based on the manufacturer's experience of the expected lifetime of the furnace. The lifetime of a furnace is affected by a number of factors, including the operational age, the average temperature of operation, the heating and cooling temperature rates, the range of temperatures of operation, the number of cycles of operation, and the type and quality of the refractory material as well as the load and type of the molten material used in the furnace. Each of these factors is subject to uncertainties that make it difficult to create accurate estimates of the expected lifetime of a furnace.

Moreover, the flow of molten material, such as molten glass, at high temperatures erodes and degrades the inner surface of the refractory material and creates a high risk for molten glass leakage through the refractory wall. A major leak of molten glass through the gaps and cracks in the furnace walls may require at least 30 days of production disruption before the furnace can be restored to operating mode because it needs to be cooled down, repaired, and fired up again. Furthermore, a leak of molten glass may cause significant damage to the equipment around the furnace and, most importantly, put at risk the health and life of workers. For these reasons, in most cases furnace overhauls are conducted at a substantially earlier time than needed. This leads to significant costs for manufacturers in terms of their initial investment and the reduced production capacity over the operational life of the furnace.

Another important issue is that the material used to build the refractory chamber of the furnace may have internal flaws not visible by surface inspection. This could translate into a shorter life of the furnace and pose serious risks during furnace operation. Accordingly, on the one hand the refractory material manufacturer would like to have a means to evaluate the material during manufacture to be able to qualify the material for furnace construction following quality standards to deliver material with no flaws. On the other hand, the customer purchasing the refractory material would like to have a means for performing internal inspections of such material before constructing a furnace.

Previous efforts have been made to use microwave signals to evaluate the status of materials such as furnace walls, as described in U.S. Pat. No. 6,198,293 to Woskov et al. and U.S. Pat. App. Pub. No. 2013/0144554 by Walton et al. However, these efforts have faced certain challenges and limitations. In particular, attempts made to use devices to evaluate the status of a furnace wall on hot furnaces have been generally unsuccessful because of the large signal losses involved in evaluating the inner surface of refractory materials, especially at relatively high frequency bands. Likewise, at relatively low frequency bands signals still experience losses and are limited in terms of the bandwidth and resolution required by existing systems. Critically, in placing system components close to the surface of the refractory material to be evaluated, spurious signal reflections make it extremely difficult to isolate the reflected signal of interest, thus further complicating the evaluation of the presence of molten material within the layers of refractory material of such furnaces. A major challenge is that furnace walls become more electrically conductive as temperature increases. Therefore, signals going through a hot furnace wall experience significant losses making the detection of these signals very challenging.

Furthermore, Ruege et al., as described in copending and co-owned U.S. patent application Ser. No. 14/226,102 titled "Material Erosion Monitoring System and Method" (the specification of which is incorporated herein by reference in its entirety), have disclosed an approach for evaluating the status of a material, based on the detection of electromagnetic waves reflected from remote discontinuities of the material. However, while this approach is effective in determining the thickness and erosion profile of different materials, including the refractory layers surrounding a furnace, to identify a flaw in the furnace walls, a major limitation may result where there is a need to determine the presence and extent of penetration of molten material within the refractory layers of the furnace. Accordingly, this approach is not able to identify or warn a user about certain leaks of molten material unless a reduction in thickness or a noticeable profile change of the refractory walls occurs. As a result, molten material may inadvertently flow throughout the furnace walls and create severe damage to the furnace without the possibility of preventing such type of situations.

Thus, there remains a need in the art for devices and methods capable of remotely evaluating the status of such refractory materials, and particularly the presence of a molten material that has leaked into one or more layers of the enclosing refractory materials, through measurements of propagating electromagnetic waves, that avoid the problems of prior art devices and methods.

SUMMARY OF THE INVENTION

An improved device and method to evaluate the status of a material by scanning an area that overlaps a region of the material under evaluation is disclosed herein. One or more aspects of exemplary embodiments provide advantages while avoiding disadvantages of the prior art. The device and method are operative to identify a leakage of a first material into a second material, such as a molten material within a furnace chamber surrounded by a refractory material, to measure the thickness of the second material, using electromagnetic waves, and to generate images. The device is designed to reduce a plurality of reflections associated with the propagation of electromagnetic waves launched into the material under evaluation, by a sufficient extent so as to enable detection of electromagnetic waves of interest reflected from remote discontinuities present in between the device and the enclosed material. Furthermore, the device can be configured to scan areas of interest in either a portable or fixed configuration, manually in a standalone mode or as part of an automated system.

The device launches electromagnetic waves into an area overlapping a material to be evaluated. The electromagnetic waves penetrate the material and reflect from discontinuities inside the different layers of the materials in between the device and the material under evaluation. The reflected electromagnetic waves are received by the device, which in turn communicates with a computer-based processor for further processing the data. The device is capable of producing quality data where the magnitude of the clutter is below the magnitude of the electromagnetic waves reflected from remote discontinuities of the material overlapping the area under evaluation. As a result, the computer-based processor may determine the presence of molten material within the refractory material in such area and generate images of the conditions of the region under evaluation, including those such as the inner walls of a furnace.

The method and device combine procedural steps with an electromagnetic wave launcher and a feeding transition section designed and adapted to reduce a plurality of reflections that significantly contribute to the clutter received by the computer-based processor. The launcher provides levels of clutter reduction by a sufficient extent so as to enable detection of electromagnetic waves of interest that otherwise might not be possible. Accordingly, the launcher may be used in evaluation of the refractory walls of hot furnaces to create a profile of the leakage of molten material into the inner walls in an operational furnace, to measure the thickness of the refractory walls as well as to determine the presence of voids, cracks, and inhomogeneous regions within such walls.

By significantly reducing the level of clutter caused by reflections and ringing of propagating electromagnetic waves, as compared to standard devices, and by determining the presence within and the level of penetration of molten material into the surrounding layers of refractory material of a furnace, the device and method are able to identify flaws and measure data to more accurately plan the maintenance required by such furnace. This results in a significant reduction of the likelihood of an unexpected leakage of molten material through the furnace wall or the need to shut down the furnace ahead of time. In addition, this also significantly reduces the risk of damage to the equipment around the furnace and the health and life of workers, contributing to an increased production capacity over the operational life of the furnace.

BRIEF DESCRIPTION OF THE DRAWINGS

The numerous advantages of the present invention may be better understood by those skilled in the art by reference to the accompanying drawings in which.

DETAILED DESCRIPTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
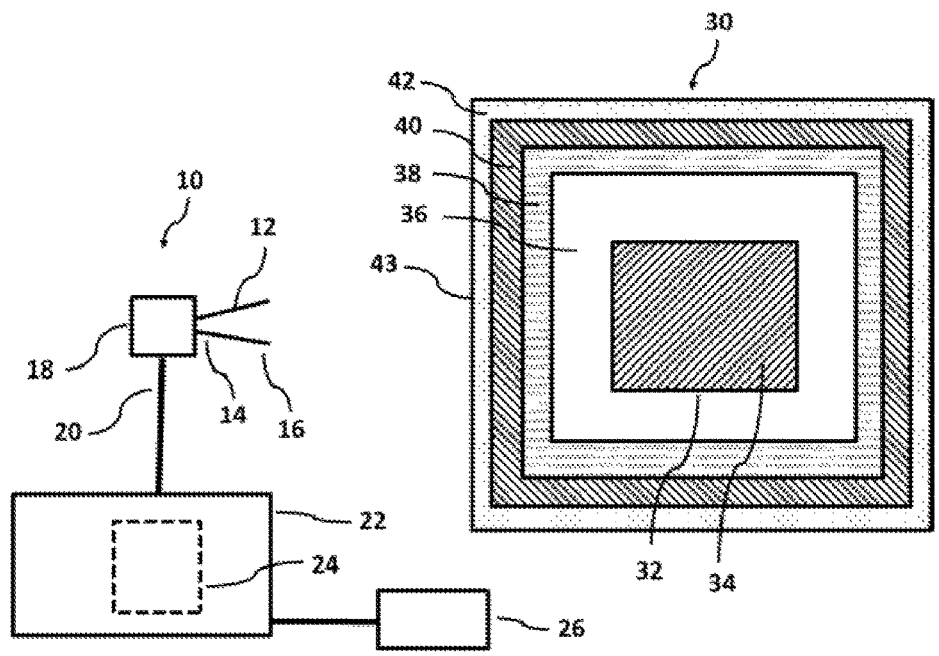
FIG. 1 shows a schematic view of a system comprising a device used to evaluate the status of a material in accordance with certain aspects of an embodiment of the invention.

In accordance with certain aspects of a configuration of the invention, a schematic view of the components of a system 10 for a typical application of evaluating a status of a material is shown in FIG. 1. The system is configured to evaluate a status of a molten material and a refractory or insulating material forming part of a furnace 30.

System 10 comprises a device consisting of a low-ringing electromagnetic (EM) wave launcher 12 having a feeding end 14 and a launching end 16. Feeding end 14 of EM wave launcher 12 includes a feeding transition section 18 electrically connected to a radiofrequency (RF) transmission line, such as a coaxial cable 20. A computer-based processor 22 is also electrically connected to coaxial cable 20. Accordingly, coaxial cable 20 is electrically connected at a first end to computer-based processor 22, and at a second end to feeding transition section 18.

Preferably, coaxial cable 20 is selected to have a physical length from computer-based processor 22 to feeding transition section 18, such that a propagation time of an EM wave propagating between first end and second end of coaxial cable 20 is larger than a propagation time of any EM wave of interest to be measured by system 10. In other words, the propagation time of the EM wave propagating throughout the length of coaxial cable 20 is larger than the propagation time of the EM wave propagating throughout EM wave launcher 12 plus the propagation time of the EM wave propagating through the walls of furnace 30. Those skilled in the art will realize that alternative ways of implementing system 10 include selecting coaxial cable 20 to be electrically very small in length or integrating feeding transition section 18 with computer-based processor 22, in which case coaxial cable 20 would not be required.

EM wave launcher 12 is typically implemented by means of an antenna with a radiation pattern primarily directed within a hemisphere and having a main radiation lobe, such that the levels of both backlobes and sidelobes is at least −10 dB with respect to the directivity of the antenna, which results in low back-lobe radiation and low scattering of RF signals transmitted and received by EM wave launcher 12.

In addition, EM wave launcher 12 is physically configured to have radiating elements having a smooth topology to prevent abrupt transitions of current flowing on EM wave launcher 12. Moreover, EM wave launcher 12 includes a feeding transition section 18 designed to minimize multiple internal reflections of EM waves. Those skilled in the art will also realize that an RF absorber material may be placed in the surroundings of EM wave launcher 12 or a variable conductivity material may be used as part of EM wave launcher 12 in order to reduce reflections, back-lobe radiation and low scattering of EM waves transmitted or received by EM wave launcher 12.

By meeting one or more of these structural and operational requirements of EM wave launcher 12, the multiple reflections of EM waves throughout the system may be significantly reduced, resulting in a low-ringing device with reduced levels of clutter, which is desirable for proper performance of system 10. However, a reduction of the multiple EM wave reflections and ringing at launching end 16, such that the ratio of the power level of an EM wave of interest to the power level of these reflections, ringing, and clutter is at least 3 dB, would be required for realizing low-ringing EM wave launcher 12. Likewise, a reduction of the multiple EM wave reflections at feeding end 14, such that the ratio of the power level of an EM wave of interest to the power level of these reflections and clutter is at least 3 dB, would be required for realizing low-ringing EM wave launcher 12. These reductions of EM wave reflections and ringing allow the system to detect and determine the level of penetration of a first material into a second material. Comparatively, the ratio of the power level of an EM wave of interest to the power level of these reflections, ringing, and clutter when using a standard performance antenna, such as a horn antenna, are typically in the order of zero dB or negative values (in dB), which makes it impossible to detect and determine the level of penetration of a first material into a second material, as well-known in the prior art. EM wave launcher 12 may be implemented by means of one or more antennas or waveguides or an array of several antennas or waveguides arranged either in a planar or non-planar configuration having one or a variety of polarizations.

During evaluation of furnace 30, EM wave launcher 12 is placed either contiguously (i.e. in physical contact) or in close proximity to outer surface 43 of furnace 30. Preferably, EM wave launcher 12 is placed contiguously to outer surface 43 during a manual scanning operation of EM wave launcher 12. However, during an automated scanning operation, launching end 16 of EM wave launcher 12 is preferably located within 0.25 inches to 2 inches of outer surface 43 of furnace 30 to expedite the scanning process. As a result, EM wave launcher 12 is designed to tolerate the required temperature range in the vicinity of outer surface 43 of furnace 30.

More particularly, the materials used to build EM wave launcher 12 are selected to allow EM wave launcher 12 to withstand such high temperatures, especially the part of launching end 16 of EM wave launcher 12 that is closer to outer surface 43 of furnace 30. Such materials should be able to withstand an ambient temperature of up to approximately 700° F., with outer surface 43 of furnace 30 reaching temperatures of up to approximately 1000° F. However, in instances where EM wave launcher 12 may be in physical contact with outer surface 43 during evaluation of furnace 30, such materials should be able to withstand temperatures of up to approximately 1500° F.

Computer-based processor 22 comprises an RF subsystem 24, signal and imaging processing subsystems, and an executable computer code or software. In this particular configuration, RF subsystem 24 comprises a tunable signal source, such as a voltage controlled oscillator or a frequency synthesizer, preferably operable in a frequency band of 0.25 GHz to 30 GHz; at least one directional coupler; a coherent detector; and at least one analog-to-digital converter.

The signal processing subsystem comprises data storage, including a solid state drive, hard drive, flash drive, a Secure Digital (SD) memory card or an Electrically Erasable Programmable Read-Only Memory (EEPROM), commercially available as well-known to those skilled in the art, and data processing algorithms. The imaging processing subsystem comprises databases, such as MySQL, an open-source relational database management system, and imaging processing algorithms. Those skilled in the art will recognize that data processing and image processing algorithms may be implemented by means of one or a combination of more than one technique. These techniques may include Fourier transform, spectral analysis, frequency- and time-domain response analyses, digital filtering, convolution and correlation, decimation and interpolation, adaptive signal processing, waveform analysis, and data windows and phase unwrapping for data processing; and time domain, back projection, delay and sum, synthetic aperture radar imaging, back propagation, inverse scattering, and super-resolution, either with or without the application of differential imaging, for image processing. System 10 also includes an image visualization subsystem 26 comprising tools for image handling and displaying. Those skilled in the art will realize that software and hardware capabilities may be added to system 10, and specifically to computer-based processor 22, for increased functionality such as to control a motion system carrying one or more components of system 10.

With continued reference to FIG. 1, it is noted that components of computer-based processor 22 have not been shown as these components are not critical to the explanation of this embodiment. Those of ordinary skill in the art will realize that various arrangements of RF subsystem 24 components may be possible and additional components, such as filters, impedance matching networks, amplifiers, non-coherent detectors and other test instrumentation may be used as different ways to implement the functionality of RF subsystem 24 of computer-based processor 22 as are known in the art.

In this configuration, furnace 30 comprises a chamber 32 containing a molten material 34, and a first layer 36, a second layer 38, a third layer 40, and a fourth layer 42 of refractory or insulating material. Furnace 30 is representative of applications used in the glass, steel, and plastic industries. In these applications, chamber 32 is typically surrounded by multiple layers of material to prevent heat loss and leakage of molten material to the outside of furnace 30 and as a safety measure to workers and equipment operating in the surroundings of furnace 30.

The inner surface of first layer 36 of refractory material is contiguous to (i.e., in physical contact with) chamber 32. Each of layers 36, 38, 40, and 42 has an outer surface and an inner surface opposite the outer surface, such that the inner surface is closer to chamber 32. However, the inner walls of chamber 32 will degrade during operation of furnace 30. The effects of this degradation include inner surface erosion, stress cracks, and refractory material diffusion into the molten material. Accordingly, molten material 34, such as molten glass, at high temperatures erodes and degrades the inner walls of chamber 32 and surrounding layers 36, 38, 40, and 42, creating a high risk for molten material leakage. Typical thickness values of refractory and insulation material of furnace walls range from 0.25 inches to 12 inches.

Figure 2:
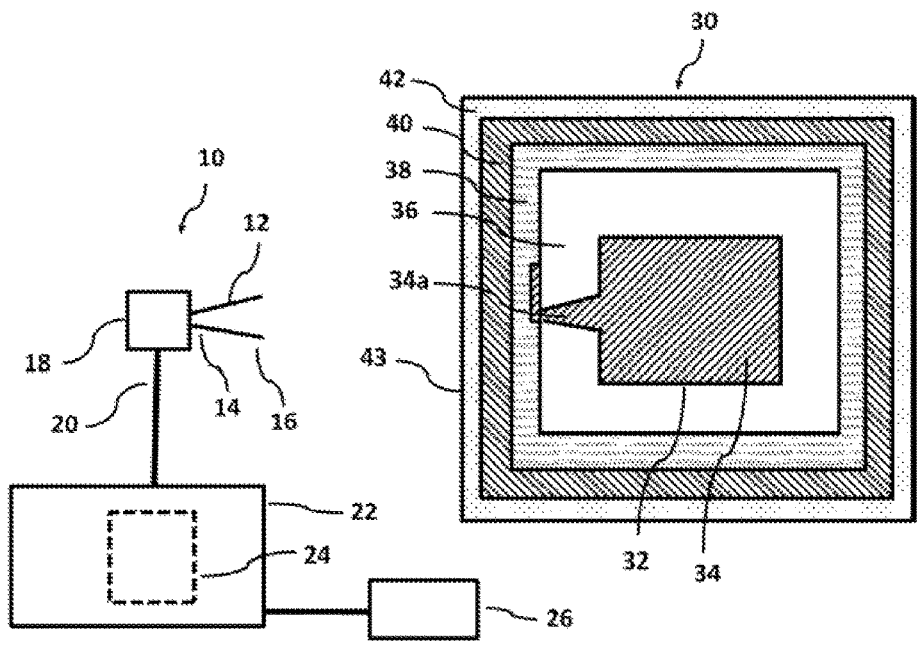
FIG. 2 shows a schematic view of the system of FIG. 1, wherein a molten material has leaked out and penetrated two layers of refractory materials.

FIG. 2 shows a cross-sectional top view of a furnace in which molten material 34a has penetrated layers 36 and 38. EM wave launcher 12 is set up to evaluate the status of molten material 34a, and more specifically to determine a presence of molten material 34a in any of the materials forming layers 36, 38, 40, and 42. In general, the location where molten material 34a has penetrated into other materials is unknown. However, EM wave launcher 12 may be placed at various locations around surface 43 of furnace 30 or may be used to scan an area of the walls of furnace 30 to evaluate the status of the materials in the corresponding regions to locate the area in which a leakage of molten material 34a has occurred. Those skilled in the art will realize that different ways of scanning an area of the walls of furnace 30 may be implemented, including mechanical and electronic scanning, performed manually or automatically.

Figure 3A:
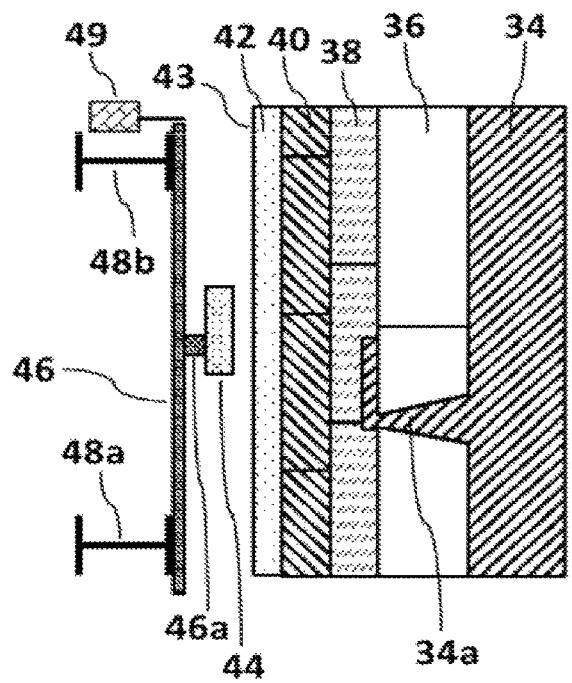
FIGS. 3A to 3C show various aspects of a system and system setups in accordance with further aspects of an embodiment of the invention.
Figure 3B:
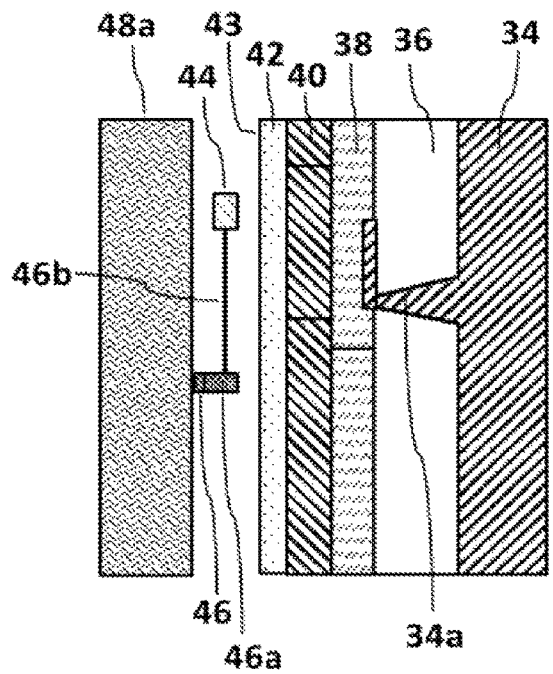
Figure 3C:
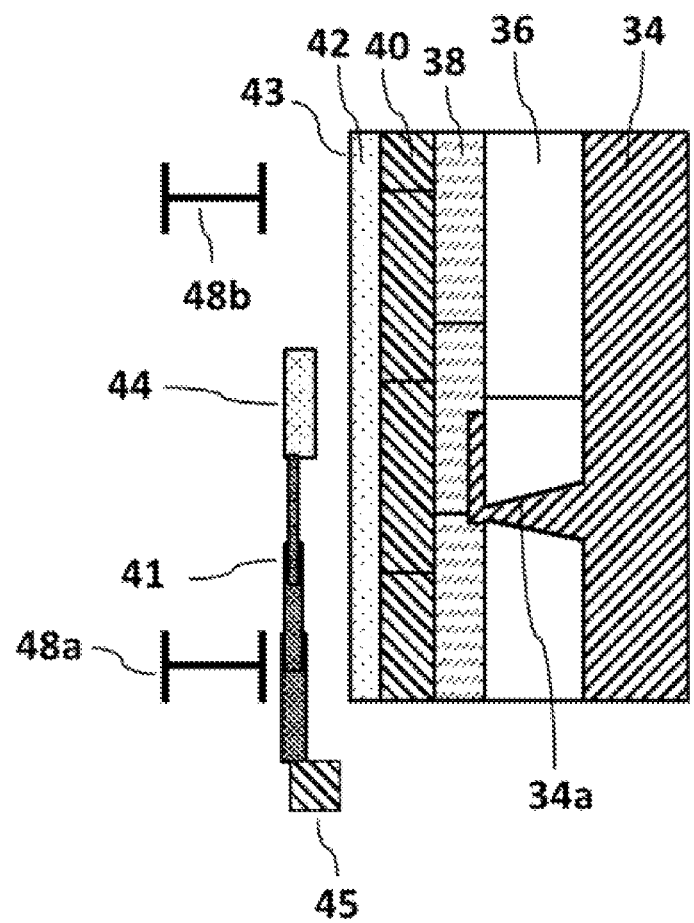

FIGS. 3A to 3C show various aspects of exemplary configurations of a scanning system using a portable device to evaluate the leakage of molten material 34a into the refractory layers 36, 38, 40, and 42 of furnace 30. In particular, FIG. 3A shows a two-dimensional top view of a compact, portable unit 44, comprising an EM wave launcher, a feeding transition section, and an RF subsystem, mounted on a first structural support 46.

In this configuration, first structural support 46 consists of a rail that runs substantially parallel to the area of the floor immediately adjacent to outer surface 43 of furnace 30. Rail 46 attaches to a second structural support of furnace 30, comprising I-beams 48a and 48b, that forms part of a structure that provides mechanical stability to furnace 30. Typically, I-beams 48a and 48b are made of steel and are separated from each other by a distance of 3 feet to 10 feet, depending on the type and size of furnace 30.

Rail 46 is preferably made of aluminum with hardened and ground steel raceways. Rail 46 runs separated from, but in close proximity and substantially parallel to, outer surface 43 of furnace 30. The dimensions of rail 46 are approximately 2 inches in width, 2 inches in height, and 14 feet in length, such that rail 46 can be mechanically attached to adjacent I-beams 48a and 48b. The separation between rail 46 and outer surface 43 must provide enough spacing for unit 44 to fit between rail 46 and outer surface 43 such that the separation between unit 44 and outer surface 43 is substantially invariable and preferably within 2 inches.

Thus, for scanning around outer surface 43, unit 44 is preferably not in physical contact with furnace 30. Additionally, the location of rail 46 may be constrained by other structural parts located adjacent to furnace 30, such as I-beams 48a and 48b. Unit 44 is mechanically attached to a side of rail 46 by means of a first extension arm 46a, which extends substantially perpendicular to rail 46 and is substantially parallel to the area of the floor immediately adjacent to outer surface 43 of furnace 30. Extension arm 46a consists of a small steel block having two edges that slide into the steel raceways of rail 46 and serves as a carriage to unit 44. In addition, extension arm 46a may have a plurality of threaded holes that allow other mechanical parts to attach to extension 46a. Alternatively, unit 44 may be attached directly underneath or above rail 46.

Rail 46 provides a guide for unit 44 to run along the length of rail 46 as part of a motion system driven by a first stepper motor 49 (e.g., Oriental Motors PK543AW) having two taper hobbed gears with a 10:1 ratio to push and pull unit 44, using an ANSI #25 roller chain system. More specifically, motor 49 drives a shaft, which couples to a steel driver sprocket of approximately 2.5-inch major diameter and a 0.25-inch pitch, by means of a steel shaft-to-sprocket coupling. Preferably, motor 49 is positioned at a location close to a first end of rail 46, such that a second end of rail 46, opposite the first end, is separated from the first end by the length of rail 46.

The roller chain engages with the driver sprocket and both ends of the roller chain attach to extension arm 46a by means of a chain attachment consisting of, for example, a screw. At the second end of rail 46, the roller chain engages with a steel idler sprocket, of about 1.7-inch major diameter and a 0.25-inch pitch, which puts tension on the roller chain and allows a smooth movement of the roller chain. As a result, the length of the roller chain is approximately twice the length of rail 46 to allow the roller chain to go back and forth once from the first end to the second end of rail 46. This arrangement provides a motion of unit 44 of about one inch along rail 46 as the motor shaft of motor 49 rotates approximately 1.26 revolutions.

Thus, as motor 49 moves the roller chain, extension arm 46a is able to slide from substantially the first end to the second end of rail 46 along the raceways of rail 46. In particular, motor 49 mechanically attaches to I-beams 48a and 48b by means of a custom clamping mechanism consisting of two steel plates on either side of each I-beam 48a and 48b and threaded rods attaching the two plates together. This configuration allows unit 44 to evaluate an area of outer surface 43 of furnace 30 along the length of rail 46. Alternatively, other means for motor 49 to move unit 44 may include a motion system based on a rack-and-pinion, a belt, a rod, or a cable.

Rail 46 may be permanently or temporarily attached to a wall of furnace 30, to I-beams 48a and 48b, or be installed just for the purpose of a single evaluation. Moreover, one or more units of rail 46 may be installed at various locations of I-beams 48a and 48b or a single unit of rail 46 may be repositioned at multiple locations for evaluation of different areas of furnace 30. As a result, unit 44 is preferably easily removable from, and installed to, rail 46.

In reference to FIG. 3B, wherein a two-dimensional side view of the exemplary configuration described in FIG. 3A is shown, a second extension arm 46b is mechanically attached, and substantially perpendicular, to first extension arm 46a and to the area of the floor immediately adjacent to outer surface 43 of furnace 30. Thus, second extension arm 46b provides a guide for unit 44 to run along an imaginary axis that is substantially parallel to outer surface 43 of furnace 30 and is substantially perpendicular to the floor immediately adjacent to outer surface 43 of furnace 30 at a substantially uniform separation from furnace 30.

In addition, extension arm 46b provides structural stability to unit 44 that reduces wavering of unit 44 while in motion. Unit 44 encloses a second stepper motor (not shown), which allows unit 44 to be pushed and pulled along the length of second extension arm 46b. This arrangement allows unit 44 to evaluate an area of outer surface 43 of furnace 30 along the length of second extension arm 46b.

Thus, the configuration shown in FIGS. 3A and 3B enables unit 44 to scan a two-dimensional area of outer surface 43 of furnace 30 to evaluate the presence of molten material 34a in the refractory layers 36, 38, 40, and 42 of furnace 30 or a status of these materials in the regions substantially perpendicular to the area scanned by unit 44. First stepper motor 49 and a second stepper motor (not shown) may be controlled by a computer-based processor by means of control wires as is well-known to those skilled in the art.

First stepper motor 49 may be placed adjacent to or within unit 44. Moreover, a two-axis stepper motor may be included in unit 44 to provide the functions of first stepper motor 49 and the second stepper motor. Furthermore, a third stepper motor (not shown) or a three-axis stepper motor may be used to enable unit 44 to move along a third axis, substantially perpendicular to surface 43, to adjust the distance between unit 44 and outer surface 43 of furnace 30 to be substantially uniform or to set up a preferred value for calibration or improved performance, typically ranging from zero (unit 44 touching outer surface 43) to 2 inches, according to the mode of evaluation selected and the EM wave launcher implemented as part of unit 44.

In particular, FIG. 3C shows a two-dimensional top view of another configuration, wherein a telescopic scanning system is used to evaluate the leakage of molten material 34a into the refractory layers 36, 38, 40, and 42 of furnace 30. This configuration comprises a compact, portable unit 44, including an EM wave launcher, a feeding transition section, and an RF subsystem mounted on a telescopic arm 41. Telescopic arm 41 is positioned such that an imaginary axis along the length of telescopic arm 41 is substantially parallel to outer surface 43 of furnace 30 and is substantially parallel to the floor immediately adjacent to outer surface 43 of furnace 30 at a substantially uniform separation from furnace 30.

In this configuration, a first structural support 45, consisting of a post, stands substantially parallel to outer surface 43 of furnace 30 and substantially perpendicular to telescopic arm 41. Telescopic arm 41 mechanically attaches to post 45, such that a two-axis stepper motor (not shown) located in a hollow section of post 45 enables motion of telescopic arm 41 along both post 45 and the imaginary axis along the length of telescopic arm 41 by means of, for example, mechanical gears. Also, other means of moving telescopic arm 41 may include a chain or belt, a pneumatic system, and a hydraulic system, all without departing from the spirit and scope of the invention.

Thus, the arrangement shown in FIG. 3C also enables unit 44 to scan a two-dimensional area of outer surface 43 of furnace 30 to evaluate the presence of molten material 34a into the refractory layers 36, 38, 40, and 42 of furnace 30 or a status of these materials in the regions substantially perpendicular to the area scanned by unit 44.

Telescopic arm 41 extends separated from, but in close proximity and substantially parallel to, outer surface 43 of furnace 30. The positioning of telescopic arm 41 and post 45 must be selected such that the separation between unit 44 and outer surface 43 is substantially invariable and preferably within 2 inches. Thus, unit 44 is preferably not in physical contact with furnace 30. However, the location of telescopic arm 41 and post 45 may be constrained by other structural parts located adjacent to furnace 30, such as I-beams 48a and 48b.

In this particular configuration, telescopic arm 41 comprises three cylindrical tubular sections that are assembled co-axially along an imaginary axis along the length and through the center of each section to form an elongated arm larger than each of these sections. One end of each section has a larger diameter of one end of an adjacent section such that a portion of one section securely fits into a portion of an adjacent section with a larger diameter. Unit 44 mechanically attaches to the section of telescopic arm 41 having the smallest diameter by means of, for example, two clamps (not shown) that fit on telescopic arm 41 and unit 44. The preferable dimensions of telescopic arm 41 are approximately 10 feet in total length with a 2-inch largest diameter and a 1-inch lowest diameter. Post 45 consists of a preferably 6-foot hollow tube having a square cross-section of 3-in side.

Preferably, telescopic arm 41 mechanically attaches to post 45 at the section of telescopic arm 41 having the largest diameter, through the use of clamps, screws, or other similarly configured fasteners that fit on telescopic arm 41 and post 45. In addition, the length and rigidity of telescopic arm 41 are preferably selected to be large enough to provide a structural stability that reduces wavering of unit 44 while in motion.

Telescopic arm 41 may be permanently attached to post 45 or a structural part of furnace 30, or be installed just for the purpose of a single evaluation. Moreover, one or more units of telescopic arm 41 may be installed at various locations of post 45 or a single unit of telescopic arm 41 may be repositioned at multiple locations for evaluation of different areas of furnace 30. Furthermore, telescopic arm 41 may attach to unit 44 and to post 45 by other means including screws, bolts, fasteners, and straps, as known in the art.

Alternatively, the structure formed by telescopic arm 41 and post 45 may be rotated 90 degrees, such that telescopic arm 41 is substantially perpendicular, and post 45 is substantially parallel, to the floor immediately adjacent to outer surface 43 of furnace 30. This arrangement will also enable unit 44 to scan a two-dimensional area of outer surface 43 of furnace 30.

Also, an additional stepper motor may be placed adjacent or within unit 44 to enable unit 44 to move along a third axis, substantially perpendicular to surface 43, to adjust the distance between unit 44 and outer surface 43 of furnace 30 to be substantially uniform or to set up a preferred value, typically ranging from zero (unit 44 touching outer surface 43) to 2 inches, according to the mode of evaluation selected by the user and the EM wave launcher implemented as part of unit 44. Also, each stepper motor may be implemented to push and pull telescopic arm 41, and as a result unit 44, by means of a number of ways, including a chain, belt, rod, or cable as known to those skilled in the art.

With continuing reference to FIGS. 3A to 3C, the capability of unit 44 to move along a third axis may allow a more efficient evaluation of furnace 30 by enabling unit 44 to avoid obstacles that may protrude from or be adjacent to outer surface 43 of furnace 30. Alternatively, unit 44 may be manually moved over different parts of furnace 30 to evaluate specific areas of outer surface 43.

In addition, unit 44 may communicate with a computer-based processor by means of a universal serial bus (USB) cable. Alternatively, an Ethernet cable or a wireless communication system, including Wi-Fi, USB-over-Wi-Fi, or Bluetooth may be used to link unit 44 and a computer-based processor for controlling the data acquisition and performing the subsequent data processing.

Figure 4A:
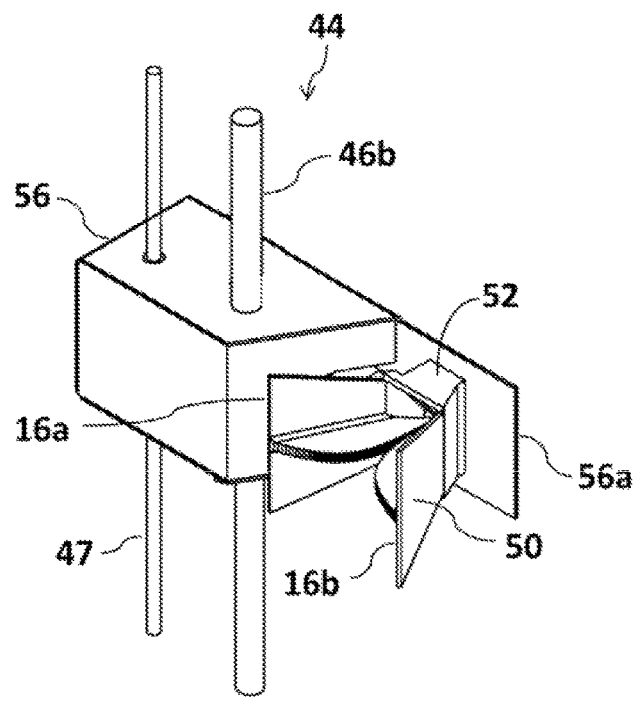
FIGS. 4A and 4B show of a compact, portable device used for material evaluation in accordance with further aspects of an embodiment of the invention.
Figure 4B:
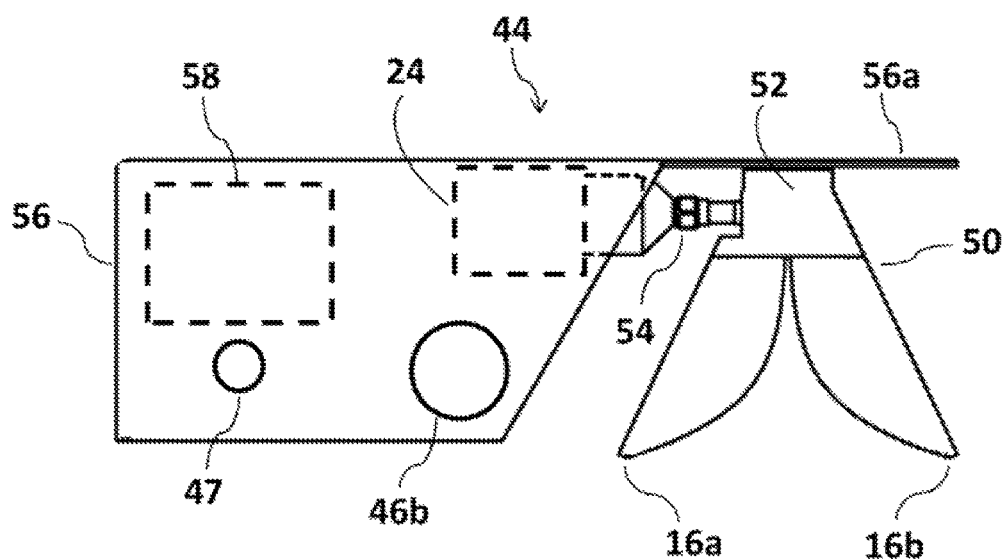

FIGS. 4A and 4B show various aspects of an exemplary configuration of a compact, portable unit 44, comprising EM wave launcher 50, feeding transition section 52, coaxial connector 54, and a housing 56, mounted on an extension arm 46b and an actuation arm 47. In particular, FIG. 4A shows a perspective view of a compact, portable unit 44 at a specific position along extension arm 46b and actuation arm 47. Extension arm 46b consists of a general purpose, circular cross-section steel rod of preferably approximately 0.5 inches in diameter and about 3 feet long to provide mechanical guidance and structural stability to portable unit 44.

Similarly, actuation arm 47 consists of a general purpose, fully threaded circular cross-section steel rod (Acme ¼-16), having a major diameter of preferably approximately 0.25 inches, 16 threads per inch, and a length of about 3 feet that attaches to a stepper motor 58 (FIG. 4B) within unit 44 to move unit 44 along extension arm 46b. Extension arm 46b and actuation arm 47 mechanically attach to extension arm 46a that rides on the raceways of rail 46. More specifically, extension arm 46b is threaded at a first end close to extension arm 46a, such that extension arm 46b screws into a first threaded hole in extension arm 46a. Likewise, actuation arm 47 screws into a second threaded hole in extension arm 46a.

FIG. 4B shows a two-dimensional top view of portable unit 44, in which EM wave launcher 50 is implemented by means of an exponentially-shaped dual-ridge, single linearly-polarized horn antenna fed thru a Sub-Miniature version A (SMA) coaxial connector and an SMA-to-N type adapter 54. In general, antenna 50 is designed to operate preferably in the frequency band from 1 GHz to 10 GHz. Ends 16a and 16b of antenna 50, which are opposite to feeding transition section 52, preferably have an approximate length of 2.9 inches and have a maximum separation of about 3.5 inches.

Feeding transition section 52 allows the transitioning of RF signals going either from coaxial connector and adapter 54 to antenna 50 or from antenna 50 to coaxial connector and adapter 54. Alternatively, EM wave launcher 50 may be implemented by means of a dual linearly-polarized antenna or an elliptically-polarized antenna.

Thus, antenna 50 meets the requirements of a low-ringing scanning device due to a smooth physical topology (exponentially-shaped ridges), an integrated feeding transition design, and structural configuration, which results in low back-lobe radiation and low scattering of RF signals transmitted and received by antenna 50.

Housing 56 is made of aluminum and encloses a stepper motor 58 (e.g., Oriental Motors PK546PA) and RF subsystem 24. Stepper motor 58 moves unit 44 in both directions along extension arm 46b by means of mechanical gears attached to stepper motor 58 and actuation arm 47. More specifically, motor 58 drives a first spur gear made of an aluminum alloy, having for example 24 teeth and a pressure angle of 20 degrees. The first spur gear drives a second stainless steel spur gear, having for example 40 teeth and a pressure angle of 20 degrees that is tapped for actuation arm 47 (Acme ¼-16). Likewise, stepper motor 58 is controlled by a computer-based processor by means of, for example, a five-wire control cable connected to a D-Sub 9, size E connector mounted on a side of housing 56 using, for example, two screws. This arrangement provides a smooth movement of unit 44 along extension arm 46b as the motor shaft rotates approximately 26.66 revolutions for unit 44 to move one inch along extension arm 46b.

In this configuration, RF subsystem 24 is implemented by means of a single-port vector network analyzer (e.g., Copper Mountain Planar R140), operating as a reflectometer, to measure the amplitude and phase of the RF signals reflected from furnace 30 after being transmitted by RF subsystem 24. Vector network analyzer 24 communicates with a computer-based processor by means of a USB cable through a USB connector mounted on a side of housing 56 using, for example, two screws.

Housing 56 consists of a box having two opposite sides substantially parallel with different dimensions. As a result, housing 56 has two opposite sides that are not parallel. The side longer in length than the corresponding opposite parallel side of housing 56 has exemplary dimensions of approximately 3 inches in width and 5 inches in length. The side shorter in length than the corresponding opposite parallel side of housing 56 has exemplary dimensions of approximately 3 inches in width and 4 inches in length. All sides of housing 56 have a thickness of about 1/16 inches. These two opposite, substantially parallel sides with different dimensions are disposed such that they are separated by a substantially perpendicular side of approximately 3 inches in width and approximately 3 inches in length, and a slanted side of approximately 3 inches in width and approximately 3.6 inches in length. The slanted configuration of one side of housing 56 is determined by the geometry of antenna 50 to maintain the compactness of portable unit 44.

In addition, housing 56 has an extension plate 56a, with exemplary dimensions of approximately 3 inches by 3 inches by ⅛ inches, to allow antenna 50 and feeding transition section 52 to mechanically attach to housing 56 by means of four bolts (not shown) and become an integral part of unit 44. Antenna 50 is centrally positioned in extension plate 56a for increased compactness of unit 44. Those skilled in the art will realize other ways of attaching antenna 50 and feeding transition section 52 to housing 56, including by means of glue, screws, soldering, clamps, and fasteners.

Thus, in this particular configuration, portable unit 44 fits within a volume defined by a box of approximately 8-inch length, 3-inch width, and 3-inch height, wherein the length of unit 44 is defined by the length of housing 56, including extension plate 56a. During normal operation, unit 44 is disposed such that an imaginary axis along the length of unit 44 is substantially parallel to both surface 43 of furnace 30 and to the area of the floor immediately adjacent to outer surface 43 of furnace 30. Also, unit 44 is disposed such that ends 16a and 16b of antenna 50 are adjacent and substantially parallel to, and preferably within 0.25 to 2 inches of, the surface under evaluation. In other words, antenna 50 is preferably not in physical contact with the surface under evaluation to facilitate the operational motion of portable unit 44. However, those skilled in the art will realize that portable unit 44 is also able to operate while ends 16a and 16b of antenna 50 are at distances smaller than 0.25 inches from the surface under evaluation.

Furthermore, housing 56 has multiple openings to allow coaxial connector 54 to directly connect to a coaxial input port of vector network analyzer 24, resulting in no need to use a coaxial cable; to provide a means for extension arm 46b and actuation arm 47 to go through housing 56, such that portable unit 44 can slide along extension arm 46b; to allow control wires of stepper motor 58 and control cables of network analyzer 24 to communicate with a computer-based processor; and to provide access to electrical cables to deliver power to stepper motor 58 and network analyzer 24.

Alternatively, battery-included devices or one or more batteries may be enclosed within housing 56 to supply power to a battery-operated stepper motor 58 or a network analyzer 24, such that access to electrical cables may not be required. Placement of RF subsystem 24 in a location that requires no need of a coaxial cable contributes to a more stable data acquisition and eliminates the adverse effects that may be caused by movement of such cable.

Figure 5:
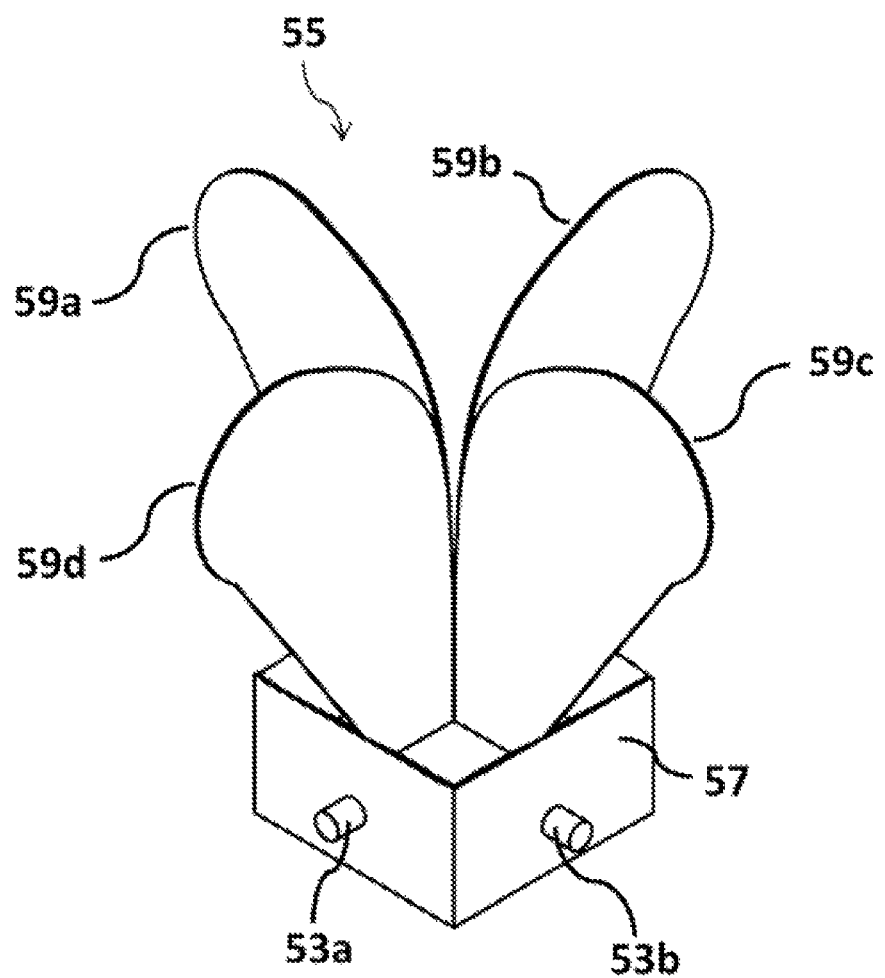
FIG. 5 shows a low-ringing electromagnetic wave launcher using a dual linearly-polarized, quad-ridge horn antenna in accordance with further aspects of an embodiment of the invention.

FIG. 5 shows a perspective view of an alternative configuration of a low-ringing EM wave launcher 55 for use with unit 44, comprising a quad-ridge, dual-polarization horn antenna having smooth edges and designed to operate in the 3 to 8 GHz frequency band. Smooth ridges 59a, 59b, 59c, and 59d contribute to improve the antenna frequency response and reduce the clutter caused by reflections and "ringing" effects of EM waves propagating along ridges 59a, 59b, 59c, and 59d of EM wave launcher 55.

In this particular configuration, each ridge 59a, 59b, 59c, and 59d has been shaped following an elliptical curve. The smooth shaping of ridges 59a, 59b, 59c, and 59d may reduce the system clutter level by up to more than 10 dB, as compared to antenna 50 of FIG. 4, at certain frequency bands of interest. Referring again to FIG. 5, EM wave launcher 55 is fed at coaxial cable connectors 53a and 53b, which transition from a coaxial cable transmission line (not shown) to the quad-ridge waveguide section by means of a cavity-backed transition section 57. EM wave launcher 55 meets the low-ringing requirements due to a smooth physical topology (elliptical ridges), a cavity-backed coaxial-to-ridge feeding design, and a structural configuration resulting in low back-lobe radiation and low scattering.

Those skilled in the art will recognize alternative ways to taper ridges 59a, 59b, 59c, and 59d to reduce the clutter caused by reflections and "ringing" effects, including by means of following an exponential function, a generally smooth transitioning function, or any combination thereof.

Figure 6:
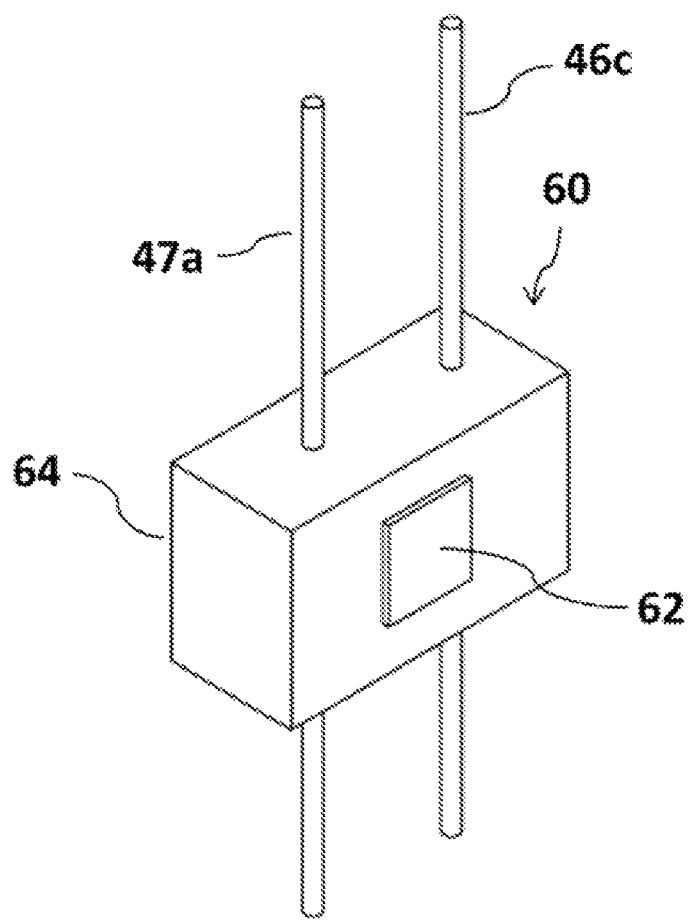
FIG. 6 shows a perspective view of a compact, portable scanning device using a planar antenna in accordance with further aspects of an embodiment of the invention.

FIG. 6 shows a perspective view of another exemplary configuration of a compact, portable unit 60, comprising an EM wave launcher 62, consisting of a planar antenna, and a housing 64 mounted at a specific position along extension arm 46c and actuation arm 47a. Extension arm 46c consists of a circular cross-section rod, made of metal, of for example approximately ¼ inches in diameter and 3 feet long that provides mechanical guidance and structural stability to portable unit 60. Actuation arm 47a consists of a metal screw of for example approximately ¼ inches in diameter and 3-foot long that attaches to a stepper motor (not shown) within unit 60 to move unit 60 along extension arm 46c.

Housing 64 is made of aluminum and consists of a box of for example approximately 4.75-inch length (longest dimension), 2-inch width (measured normal to the surface under evaluation), and 3-inch height, wherein the length and height of portable unit 60 are defined by the length and height of housing 64, respectively. The overall width of unit 60 is defined by the width of housing 64 and the width of planar antenna 62. All sides of housing 64 have a thickness of for example about ¹⁄₁₆ inches.

Also, housing 64 comprises multiple openings, and encloses a stepper motor, an RF subsystem (not shown), and mechanical, electrical, and control parts similar to those described in the configuration shown in FIG. 4B. This arrangement allows a computer-based processor to control data collection and motion of portable unit 60. Portable unit 60 also comprises a feeding transition section and a coaxial connector to electrically connect planar antenna 62 to the RF subsystem.

In general, planar antenna 62 may be mechanically attached to, and centrally positioned on, a side of housing 64 by means of four bolts (not shown). Likewise, planar antenna 62 is designed to operate preferably in the frequency band from 1 GHz to 10 GHz as an elliptically- or a single or dual linearly-polarized antenna. Those skilled in the art will realize other ways of attaching planar antenna 62 to housing 64, including by means of glue, screws, soldering, clamps, and fasteners.

During normal operation, unit 60 is disposed such that an imaginary axis along the length of unit 60 is substantially parallel to the surface under evaluation and to the area of the floor immediately adjacent to the surface under evaluation. Also, unit 60 is disposed such that planar antenna 62 is adjacent and substantially parallel to, and preferably within 0.25 to 2 inches of, the surface under evaluation. In other words, planar antenna 62 is preferably not in physical contact with the surface under evaluation.

Referring to FIGS. 4 to 6, those skilled in the art will realize alternative arrangements and locations of EM wave launchers 50, 55, 62 and components enclosed within or attached to housings 56, 64, including relocation of components outside of housings 56, 64, such that portable units 44, 60 may take different geometrical forms and smaller sizes without affecting or limiting the performance of portable units 44, 60.

Figure 7A:
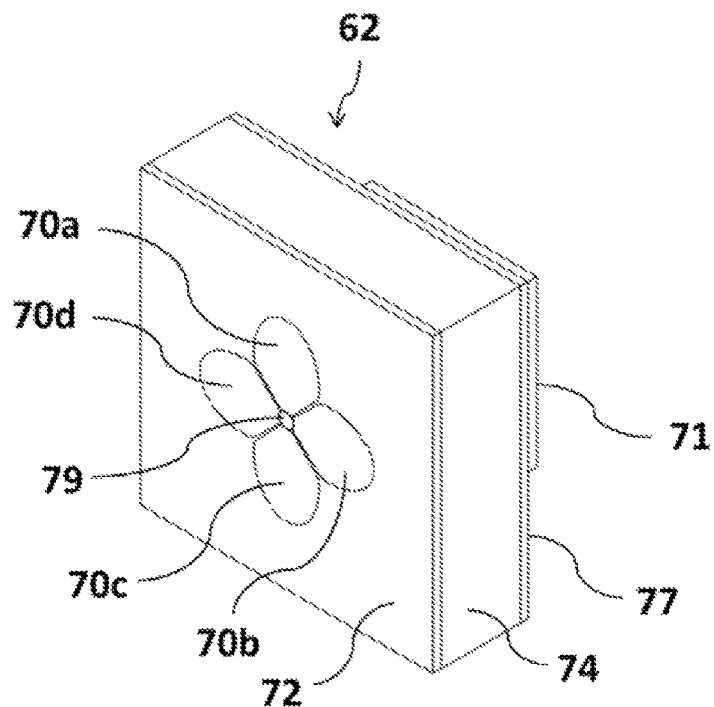
FIGS. 7A and 7B show various aspects of an electromagnetic wave launcher using a broadband cross-dipole in accordance with further aspects of an embodiment of the invention.
Figure 7B:
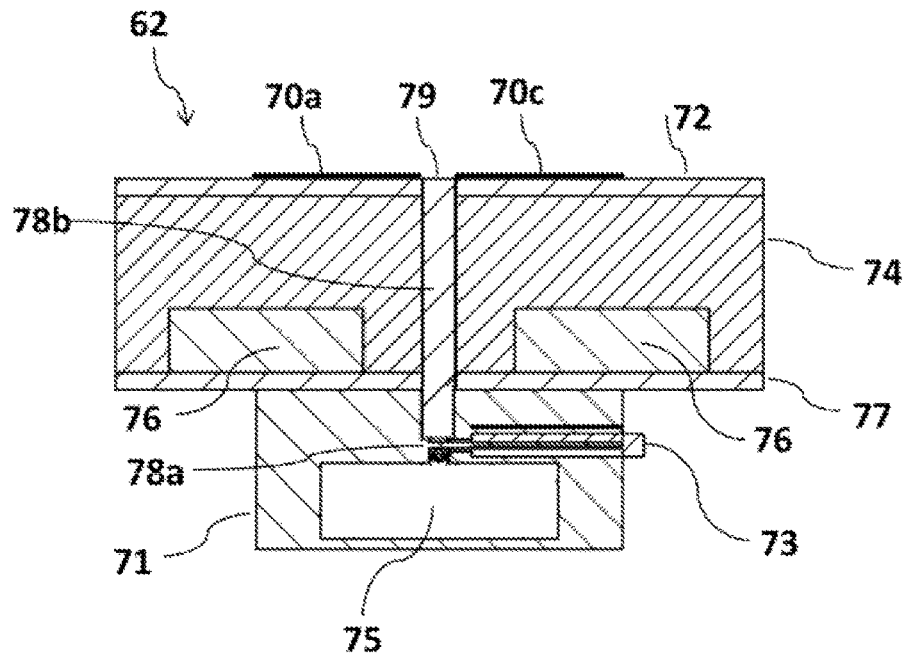

In particular, FIGS. 7A and 7B show various aspects of a low-ringing EM wave launcher 62 for use with portable units 44 and 60 comprising a broadband, dual-polarization cross-dipole, planar antenna designed to operate in the 3 to 10 GHz frequency band, in accordance with certain aspects of the invention. More specifically, FIG. 7A shows a perspective view of planar antenna 62, which includes four dipole arms 70a, 70b, 70c, and 70d, substantially identical to each other, and disposed on a layer of a first dielectric substrate 72, having approximate dimensions of for example 2.3 inches in length and height and 0.05 inches in width. A second dielectric substrate 74 of about the same length and height as substrate 72, disposed substantially parallel and adjacent to substrate 72, separates substrate 72, by approximately 0.75 inches, from a third dielectric substrate 77. Substrate 77 has the same dimensions of substrate 72 and is adjacent to feeding transition section 71.

Each dipole arm 70a, 70b, 70c, and 70d of planar antenna 62 consists of a thin layer of conductive material having an oval shape with a maximum width of approximately for example 0.5 inches to provide a broadband frequency response. Dipole arms 70a, 70b, 70c, and 70d of planar antenna 62 are arranged on substrate 72, having one end of each dipole arm 70a, 70b, 70c, and 70d slightly modified to converge around a center 79. Thus, dipole arms 70a, 70b, 70c, and 70d of planar antenna 62 are arranged in a way that resembles a 4-petal flower, such that the distance from center 79 to the farthest point of each dipole arm 70a, 70b, 70c, and 70d is approximately for example 0.7 inches.

FIG. 7B shows a two-dimensional cross-sectional side view of planar antenna 62, in which feeding transition section 71 enables a transitioning from a coaxial transmission line 73 to a twin-line transmission line 78b by means of a feed point 78a backed by a cavity 75. As a result, dipole arms 70a, 70b, 70c, and 70d are directly fed at center 79 by a dual linearly-polarized twin-line transmission line 78b.

Feeding transition section 71 is made of a hollow block of conductive material of approximately 1.4 inches in length and height and 0.5 inches in width. Thus, the overall width of planar antenna 62, including feeding transition section 71 is about for example 1.35 inches. Cavity 75, within feeding transition section 71, has a box shape with approximate dimensions of for example 0.9 inches in length and height and 0.2 inches in width. Each side of cavity 75 is substantially parallel to a corresponding side of the block forming feeding transition section 71. One side of cavity 75 has a center opening that is positioned at the location of feed point 78a to improve the performance of feeding transition section 71. In addition, feeding transition section 71 has an opening on one side just large enough to allow coaxial transmission line 73 to access feed point 78a.

Preferably, planar antenna 62 also comprises a piece of RF absorber material 76 disposed on substrate 77, and within substrate 74, in a way that RF absorber material 76 is substantially underneath each of dipole arms 70a, 70b, 70c, and 70d, such that the four pieces of RF absorber material 76 form a square annular-ring. The presence of absorber material 76 significantly attenuates the RF signals transmitted by dipole arms 70a, 70b, 70c, and 70d into substrate 74, resulting in a substantial reduction of the overall system clutter. Also, substrate 77 provides structural support to absorber material 76. Alternatively, air may replace second dielectric substrate 74 and a conductive material, such as a metal plate, may replace RF absorber material 76.

Thus, planar antenna 62 meets the requirements of a low-ringing scanning device due to a smooth physical topology (oval shape) of dipole arms 70a, 70b, 70c, and 70d, a cavity-backed twin-line transmission line feeding design, and a structural configuration, including absorber material 76, which results in low back-lobe radiation and low scattering of RF signals transmitted and received by planar antenna 62.

Figure 8A:
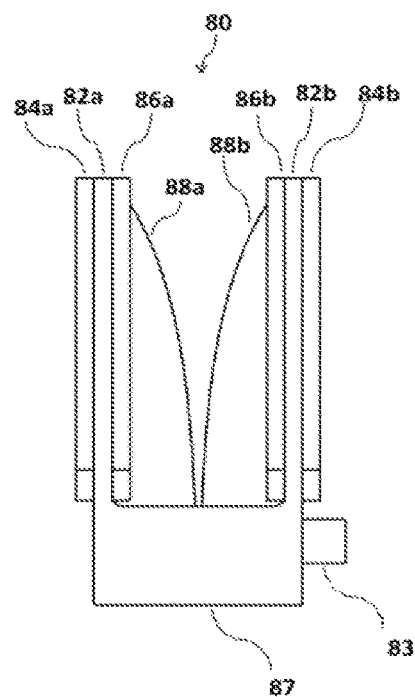
FIGS. 8A and 8B show various aspects of an electromagnetic wave launcher using a linearly-polarized, dual-ridge horn antenna with an absorber material in accordance with further aspects of an embodiment of the invention.
Figure 8B:
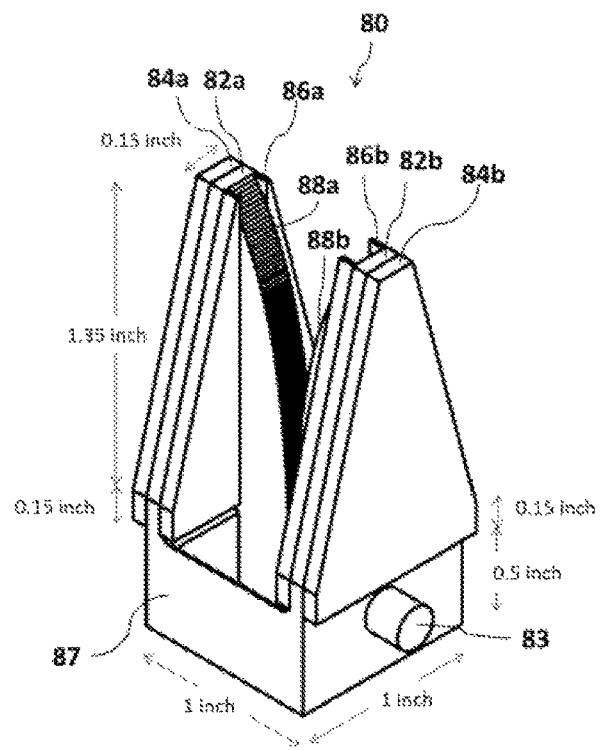

FIGS. 8A and 8B show various aspects of another exemplary configuration of a low-ringing EM wave launcher 80 for use with portable units 44 and 60, comprising a dual-ridge, linearly-polarized horn antenna having smooth edges and designed to operate in the 3 to 18 GHz frequency band. EM wave launcher 80 comprises a first side 82a and a second side 82b, identical in dimensions and made of a highly conductive material, having an isosceles triangular shape with for example a 0.15-inch truncation at each vertex. Sides 82a and 82b are each approximately for example 0.1-inch thick, separated by about 0.8 inches, and substantially parallel to one another. Exponentially-shaped ridges 88a and 88b extend toward one another from and substantially perpendicular to sides 82a and 82b, respectively. At a cavity-backed transition section 87, ridges 88a and 88b are at their closest point, separated by approximately for example 0.02 inches. The separation between ridges 88a and 88b increases as each gets farther from transition section 87 until merging with sides 82a and 82b, respectively. Each ridge 88a and ridge 88b follows a natural exponential curve, such that the distance, D, from each ridge 88a to side 82a and from ridge 88b to side 82b is approximately given by:

$$D \text{ (in inches)} = 0.01*(\exp(2*d)-1)+0.008; \text{ for } 0<d<1.8 \text{ inches}$$

where "d" represents the distance (in inches) from the merging point of side 82a or 82b with ridge 88a or 88b to the projection of a point along ridge 88a or 88b onto side 82a or 82b, respectively. In particular, FIG. 8A illustrates a side view of EM wave launcher 80, whereas FIG. 4B shows a perspective view of EM wave launcher 80.

In a preferred configuration, EM wave launcher 80 also comprises a layer of a magnetic absorber material 84a, 84b, 86a, 86b, such as the Emerson & Cuming ECCOSORB MCS, having a similar footprint to sides 82a and 82b and at least approximately 0.1 inches in thickness. Layers 84a and 86a are disposed contiguously and substantially parallel to side 82a. Likewise, layers 84b and 86b are disposed contiguously and substantially parallel to side 82b. In other words, side 82a is sandwiched in between layers of absorber material 84a and 86a, and side 82b is sandwiched in between layers of absorber material 84b and 86b.

More preferably, layers 84a, 84b, 86a, and 86b are flexible, magnetically loaded, high-loss rubber absorbers and are attached to sides 82a and 82b by means of a pressure sensitive adhesive or silicone-based adhesive that is commercially available. Material 84a, 84b, 86a, and 86b and smooth ridges 88a and 88b contribute to improving the antenna frequency response and may reduce the clutter caused by reflections and "ringing" effects of EM waves propagating along ridges 88a and 88b of EM wave launcher 80, by up to more than 15 dB, as compared to antenna 50 of FIG. 4, at the frequency bands of interest.

With continued reference to FIGS. 8A and 8B, EM wave launcher 80 is fed at coaxial connector 83, which transitions from a coaxial cable transmission line (not shown) to the dual-ridge waveguide section by means of cavity-backed transition section 87, as well-known in the prior art. Cavity-backed transition section 87 has dimensions for example of approximately 1-inch long, 1-inch wide, and 0.5-inch height. The total length of EM wave launcher 80 is approximately for example 2 inches. EM wave launcher 80 meets the low-ringing requirements due to a smooth physical topology (exponential ridges), a cavity-backed coaxial-to-ridge feeding design, and a structural configuration resulting in low back-lobe radiation and low scattering.

Those skilled in the art will recognize that alternative EM wave absorber materials may be used to reduce the clutter caused by reflections and "ringing" effects, including by means of a material having a variable conductivity, an EM metamaterial, a radiofrequency absorber material, or any combination thereof configured in different geometrical arrangements. In addition, one or a combination of more than one of these materials may be used as part of EM wave launcher 80, including replacing a piece of EM wave launcher 80, to reduce the clutter caused by reflections and "ringing" effects.

Alternatively, more than one EM wave launcher 80 may be arranged in a linear or in a two-dimensional array to electronically scan larger areas of a material under evaluation with less or no need to mechanically move EM wave launcher 80; perform faster evaluations; or operate a plurality of EM wave launchers in a multistatic mode, wherein more than one EM wave launchers 80 launch an EM wave, more than one EM wave launchers 80 receive an EM wave, or a combination thereof. Accordingly, the plurality of EM wave launchers 80 may be arranged in various operational configurations, including a fixed configuration to evaluate or monitor over time a region of a material and a movable configuration as part of either a portable device mounted on a moving apparatus or a handheld device, for both manual and automated operation.

Those skilled in the art will also realize that when using more than one EM wave launcher, multiple radiofrequency switches, duplexers, or equivalent devices may be required. More specifically, such multiple components may be required to select the particular EM wave launcher that will transmit or receive an EM wave, and more importantly to synchronize when each EM wave launcher will transmit or receive the corresponding EM wave for a proper multistatic operation as well-known in the prior art.

Figure 9:
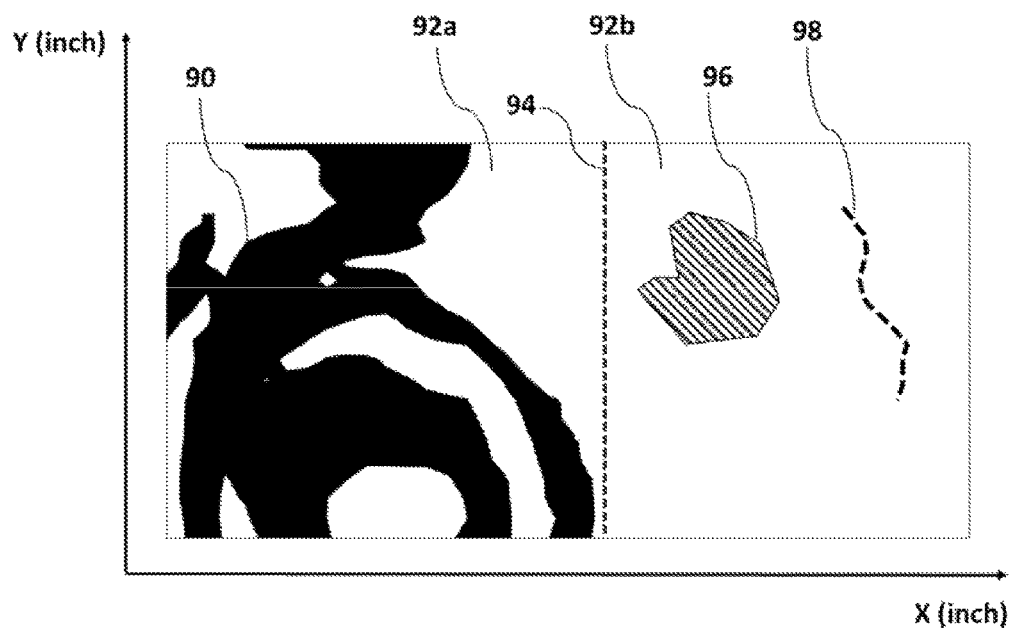
FIG. 9 shows a snapshot image of the results of an evaluation of the status of a material in accordance with an embodiment of the invention.

In order to visualize the results of the evaluation of a material, including the presence of a first material within a second material and the status of a material, one or more images may be generated to create a two-dimensional (2D) or a three-dimensional (3D) visualization. In a preferred configuration, a plurality of 2D images are generated to create a 3D visualization of the multiple layers of material surrounding a furnace chamber containing molten material. Accordingly, FIG. 9 shows a snapshot image of actual results of an evaluation of the status of a material in accordance with an embodiment of the invention. The snapshot image represents a cross-sectional view, substantially parallel to the outer surface of the furnace corresponding to the region under evaluation, at a specific position in between such outer surface and the furnace chamber. In other words, the snapshot image is taken within one of the refractory layers surrounding the furnace chamber.

More specifically, FIG. 9 shows a first material 90, consisting of molten material, present within a first region 92*a* of a second material, consisting of a refractory material. A second region 92*b* of refractory material is separated from first region 92*a* by joint 94. This is representative of a typical furnace built with refractory bricks, wherein first and second regions 92*a* and 92*b* are each part of different and adjacent bricks of refractory material. According to the results shown in FIG. 9, molten material 90 has leaked outside of the furnace chamber and is present in first region 92*a*. Therefore, molten material 90 should have also penetrated into all layers of refractory material in between first region 92*a* of refractory material and the furnace chamber.

In addition, the snapshot image of FIG. 9 shows possible results of an evaluation of the status of a material, consisting of a void 96 and a crack 98 in second region 92*b* of the refractory material. Void 96 and crack 98 represent anomalies in the refractory material and may be indicative of wear, tear, or defects in the furnace that may need to be monitored or addressed to prevent additional problems. Accordingly, FIG. 9 shows a 2D map of anomalies corresponding to a condition and a status of a material in a Cartesian coordinate system. The X-axis represents the horizontal position along an axis substantially parallel to both the outer surface of the furnace and the area of the floor immediately adjacent to the outer surface of the furnace. The Y-axis represents the position along an axis substantially perpendicular to the area of the floor immediately adjacent to the outer surface of the furnace.

Therefore, FIG. 9 may provide the status and specific location of any anomaly of the furnace on a plane for the region under evaluation in between the outer surface of the furnace and the furnace chamber. Moreover, a 3D mapping of such region may be visualized by combining a plurality of substantially parallel 2D images. A 3D image not only may provide the specific location, but also the extent of an anomaly. In addition, the erosion profile and thickness of a particular layer of a material may be determined. This is of key importance to estimate the remaining life of a furnace or when a repair of a furnace may be needed to prevent major problems.

Those skilled in the art will recognize that different imaging techniques may be used to visualize the status of a material in a 2D or 3D representation, including the use of different colors, color grades, and types of plots, corresponding to the region under evaluation.

Figure 10:
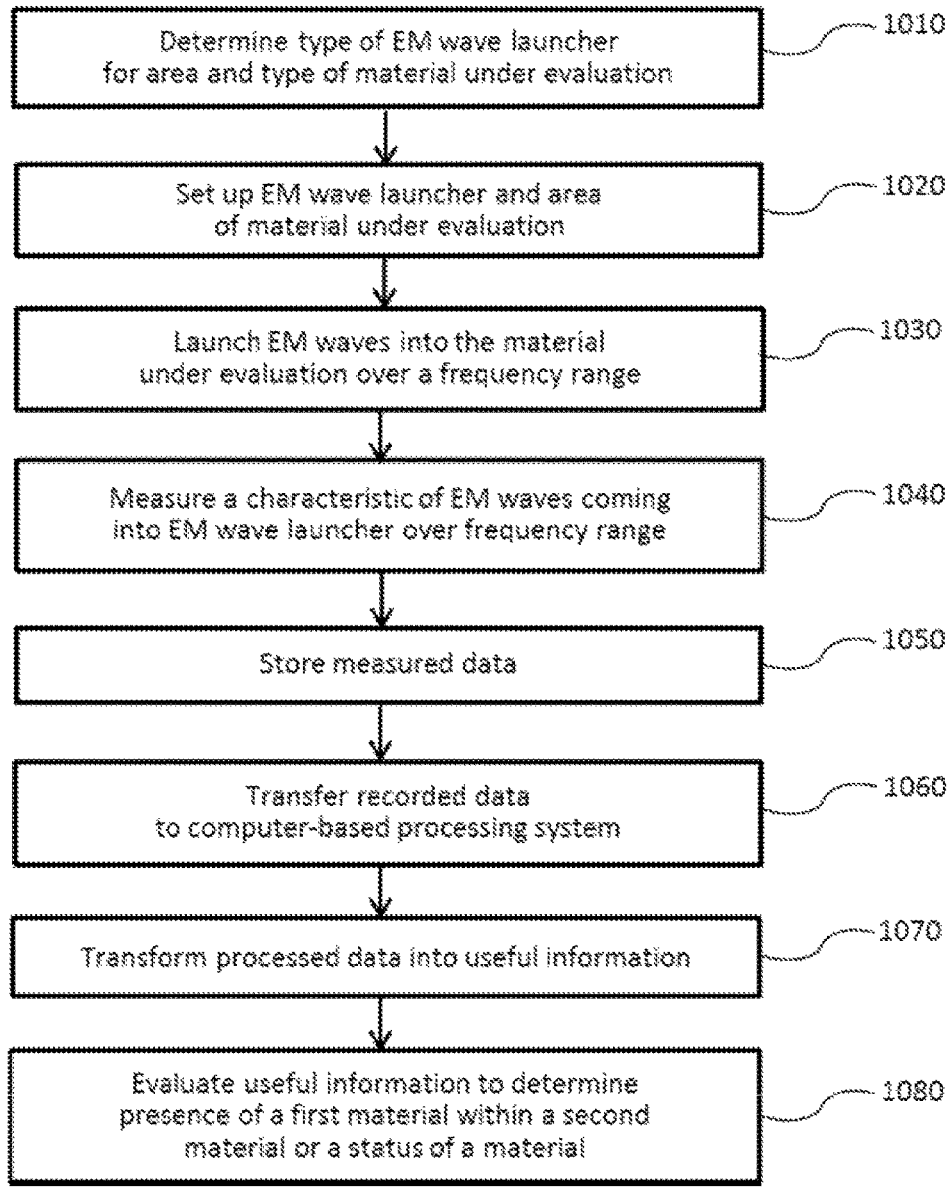
FIG. 10 shows a schematic view of a method for evaluating the status of a material.

Regarding each of the above-described configurations, a method depicted in FIG. 10 for determining a status of the subject material under evaluation, including the presence of a first material within a second material, using EM waves, may be performed according to the following:

1. At step 1010, determining the type of low-ringing EM wave launcher to be used for evaluating the status of the region of the material under evaluation, according to the size and accessibility to such region, type of material, and user needs. A fixed device mounted on a supporting structure may be preferred for closely monitoring an area smaller than or equal to the spot size of the EM wave launcher at the area of interest. A handheld device may be preferred for a quick evaluation of multiple regions of relative small or medium size as compared to the spot size of the EM wave launcher at the area of interest. In addition, a handheld device may allow a user to reach areas that are difficult to access due to the presence of structural or external objects in the vicinity of the region to be evaluated. A portable device mounted on a movable supporting structure may be preferred for scanning large regions partly or in its entirety. In addition, the type of device used may depend on the capability of using more than one EM wave launcher or performing electronic or mechanical scanning 2. Next, at step 1020, setting up the EM wave launcher by placing a launching end of the EM wave launcher separated, preferably within two inches, from the outer surface of the physical structure adjacent and as close as possible to the region of the first material to be evaluated, such that upon operation of the EM launcher, EM waves are launched into such region of the first material under evaluation.

3. Next, at step 1030, launching EM waves from the EM launcher into the outer surface of the material under evaluation by exciting EM wave propagating modes inside the EM wave launcher over a transmit frequency range, and correspondingly generating EM waves propagating inside the EM wave launcher from a feeding end of the EM wave launcher to the launching end of the EM wave launcher, over the frequency range.

4. Next, at step 1040, measuring a set of data pertaining to a characteristic of the EM waves coming into the EM wave launcher, as a result of the propagation of the EM waves launched by the EM wave launcher into the outer surface of the material under evaluation. This measured data may include the amplitude and the phase, one or more scattering parameters, time of arrival, real or imaginary components, and correlation of the EM waves, using or not a pre-determined reference EM wave or signal.

5. Next, at step 1050, storing the set of data pertaining to the measured characteristic of the EM waves coming into the EM wave launcher. The measured set of data may be stored locally in either the portable, fixed-mounted, or handheld device used or in an external component, such as a storage unit upon transmission of the data wirelessly or by wire.

6. Next, at step 1060, transferring the recorded set of data to a computer-based data processor.

7. Next, at step 1070, transforming the transferred set of data into useful information corresponding to the status of the material under evaluation, including the presence of the first material within the second material. This step may include processing the data in or transforming the data into time domain, frequency domain, spatial domain, or image domain; calibrating and normalizing the data; filtering the undesired effects caused by multiple reflections associated with the propagation of EM waves through discontinuities between two materials or between the EM wave launcher and a material, or the effects of known objects, structural components, or interfaces of material, using the computer-based data processor along with the corresponding software, mathematical algorithms or imaging transformation techniques.

This useful information may be presented as a list, table, curve, bar graph, plot, video, or a plurality of two-dimensional, frontal-view images (at multiple distances from the EM wave launcher) of the region of the material under evaluation, such that other images can be created corresponding to different views of the second material, including two-dimensional side-view images and three-dimensional images.

8. Last, at step 1080, evaluating the results of the processed data to determine the regions wherein the first material under evaluation has penetrated the second material, including the location and extent of the penetration or to determine the status of a material, such as the leakage of the first material into the second material and thickness of the second material under evaluation by calculating the distance between the outer, near surface and the inner, remote surface of the second material under evaluation. The thickness of the second material may be indicative of the level of degradation or erosion of the second material or the presence of weak regions in the second material that may lead the first material to pass through the second material.

Those of ordinary skill in the art will recognize that the steps above indicated can be correspondingly adjusted for specific configurations and other constraints such as measurement equipment, operating frequency band, type of EM wave launcher, operational conditions, surrounding environment, and available area and location for implementation of the material evaluation system for a given application. In particular, measurements of the amplitude and the phase of EM waves, required over a high dynamic range (in some cases in excess of 90 dB), may be accomplished in multiple ways, such as through use of a network analyzer to measure the S11 scattering parameter over a frequency band, using a monostatic configuration (a single device to both launch EM waves and receive EM waves) or to measure the S21 scattering parameter, over a frequency band, using a bistatic configuration (a first device to launch EM waves and a second device to receive EM waves) or a multistatic configuration (more than one device to launch EM waves, more than one device to receive EM waves, or a combination thereof). In other cases, time-domain measurements may be performed by transmitting a pulse with a duration of about one nanosecond and measuring the magnitude of the reflected pulse in the time domain.

Those skilled in the art will also recognize that the steps above indicated can be correspondingly adjusted for specific architectures of the chamber containing the first material and multilayer structures comprising different materials external to the chamber, as well as other constraints, including the number of structural layers, type and dimensions of materials, operating frequency band, type of EM wave launcher, and accessibility and available area for location of the EM wave launcher.

In particular, for a multilayer structure disposed in between the EM wave launcher and the chamber, the described method may be used to create images of different views, including two-dimensional frontal and side views and three-dimensional perspective views, of one or more layers corresponding to the region under evaluation. As such, the method may also be used to determine the parts of any layer of material that have been penetrated by the first material, including the location and extent of the penetration, as well as to determine the thickness, homogeneity, discontinuities, and surface characteristics of a material. In a multilayer configuration, typically additional data processing is required. However, there is no need to perform additional measurements or data collection procedures no matter what is the actual number of layers in between the second material and the chamber or between the EM wave launcher and the chamber.

Additionally, those skilled in the art will realize that, while evaluating the calibrated distance domain data, intermediate peak values over the clutter plus noise level may appear between the reference point associated with an EM wave reflected from the outer, near surface of the material under evaluation and the peak value associated with an EM wave reflected from the inner, remote surface of the material under evaluation; it being understood that the intermediate peak values may be associated with flaws of the material under evaluation existing between the outer, near surface of the material under evaluation and the inner, remote surface of the material under evaluation.

Furthermore, the calibration of the time domain data to distance domain data may include the subtraction of the delay time (distance) associated with the EM wave launcher and cables. Moreover, the frequency dispersion effects of the EM wave launcher and the material under evaluation may be removed, if necessary, by normalizing the measured data of the material under evaluation with respect to another set of measured data corresponding to a reference configuration, by way of non-limiting example, of a known characteristic and thickness of a material similar to the material under evaluation, through processes well known to those skilled in the art.

Likewise, those skilled in the art will realize that diverse methods may be used to determine the thickness of each layer of material or to identify the presence of the first material within any of the other materials. These methods include relying on the known properties of the first material and the other materials, having a database with signal-processed and or image signatures of the first material and the other materials, and the specific physical and dimensional arrangement of the materials in the region under evaluation. In addition, a means to generate an image may be implemented by using one or more imaging techniques, comprising time domain, back projection, delay and sum, synthetic aperture radar imaging, back propagation, inverse scattering, and super-resolution, either with or without the application of differential imaging.

The method and various embodiments have been described herein in an illustrative manner, and it is to be understood that the terminology used is intended to be in the nature of words of description rather than of limitation. Any embodiment herein disclosed may include one or more aspects of the other embodiments. The exemplary embodiments were described to explain some of the principles of the present invention so that others skilled in the art may practice the invention. Obviously, many modifications and variations of the invention are possible in light of the above teachings. The present invention may be practiced otherwise than as specifically described within the scope of the appended claims and their legal equivalents.

We claim:

1. A device for evaluating a status of a first material enclosed by a second material, comprising:
   a. a housing mechanically attached to a first supporting structure;
   b. an electromagnetic wave launcher having a feeding end and a launching end, wherein said feeding end includes a feeding mechanism configured to excite an electromagnetic wave able to propagate through said electromagnetic wave launcher, wherein said launching end is configured to transmit said electromagnetic wave to a region external to said electromagnetic wave launcher and is physically structured to reduce a plurality of reflections and to reduce a ringing of said electromagnetic wave propagating through said launching end by a sufficient extent so as to enable detection of an electromagnetic wave of interest reflected from a presence of said first material within said second material, and wherein said electromagnetic wave launcher is adapted to delay receipt of said electromagnetic wave of interest reflected from said presence of said first material within said second material by a time period sufficient to distinguish between said reflected electromagnetic wave of interest and a spurious electromagnetic wave reflected from a discontinuity of said second material; and
   c. a feeding transition section, wherein said feeding end adapts a radiofrequency signal from and to said electromagnetic wave, and wherein said feeding end is configured to reduce a plurality of reflections of said excited electromagnetic wave at said feeding end by a sufficient extent so as to reduce a level of clutter otherwise present in said electromagnetic wave launcher;
   wherein said electromagnetic wave launcher is further physically configured so as to reduce a level of clutter otherwise present in said electromagnetic wave launcher by at least 10 dB; and
   wherein said housing mounts said electromagnetic wave launcher and said feeding transition section.

2. The device of claim 1, wherein said electromagnetic wave launcher, said feeding transition section, and said housing are configured as a portable unit.

3. The device of claim 1, wherein said first supporting structure comprises a handheld element to enable a handheld configuration for scanning an area to evaluate said status of said first material.

4. The device of claim 1, wherein said first supporting structure comprises a first arm that guides a motion of said device in a first dimension along a length of said first arm and attaches to a second supporting structure.

5. The device of claim 4, further comprising a third supporting structure having a second arm that guides a motion of said device in a second dimension along a length of said second arm, wherein said third supporting structure attaches to said first supporting structure, and wherein said first arm of said first supporting structure is substantially perpendicular to said second arm of said third supporting structure.

6. The device of claim 1, wherein said first supporting structure comprises a telescopic arm.

7. The device of claim 1, further comprising a radiofrequency subsystem to detect and measure said electromagnetic waves of interest, wherein said radiofrequency subsystem is installed in said housing and is capable of generating and detecting an electromagnetic wave in a frequency range of between 0.25 and 30 GHz.

8. The device of claim 1, further comprising a radiofrequency subsystem to detect and measure said electromagnetic waves of interest, wherein said radiofrequency subsystem is installed in said housing and is capable of generating and detecting a plurality of electromagnetic waves associated with a time-domain pulse with a duration in the range of between 0.1 and 10 nanoseconds.

9. The device of claim 1, wherein said electromagnetic wave launcher comprises a radiofrequency absorber material able to substantially absorb electromagnetic energy, wherein said radiofrequency absorber material is positioned to reduce said plurality of reflections and to reduce said ringing of said electromagnetic wave propagating through said electromagnetic wave launcher.

10. The device of claim 9, wherein said radiofrequency absorber material comprises at least one layer of absorbing material disposed adjacent to said launching end of said electromagnetic wave launcher.

11. The device of claim 1, wherein said launching end of said electromagnetic wave launcher has at least one smooth edge.

12. The device of claim 1, further comprising a motor to provide a motion of said device.

13. The device of claim 1, further comprising a plurality of electromagnetic wave launchers, wherein at least one of said plurality of electromagnetic wave launchers transmits said electromagnetic wave.

14. The device of claim 13, wherein said plurality of electromagnetic wave launchers are configured to electronically scan an area to evaluate said status of said first material.

15. The device of claim 1, wherein said device is configured to generate a result of an evaluation of an element selected from the group consisting of said status of said first material and a status of said second material, and wherein said result is represented by an image.

16. The device of claim 1, wherein said feeding transition section comprises a cavity-backed feeding pin.

17. The device of claim 1, wherein said EM wave launcher further comprises a material having a variable conductivity.

18. The device of claim 1, wherein said launching end of said electromagnetic wave launcher further comprises at least one smooth edge that follows a shape of a curve through an outer-most portion of said launching end.

19. The device of claim 18, wherein said curve extends from an interior side of said edge through said outer-most part of said launching end and to an exterior side of said edge.

20. A method for evaluating a status of a first material enclosed by a second material, comprising:
   a. providing a housing mechanically attached to a first supporting structure; an electromagnetic wave launcher having a feeding end and a launching end, wherein said feeding end includes a feeding mechanism configured to excite an electromagnetic wave able to propagate through said electromagnetic wave launcher, wherein said launching end is configured to transmit said electromagnetic wave to a region external to said electromagnetic wave launcher and is physically structured to reduce a plurality of reflections and to reduce a ringing of said electromagnetic wave propagating through said launching end by a sufficient extent so as to enable detection of an electromagnetic wave of interest reflected from a presence of said first material within said second material, and wherein said electromagnetic wave launcher is adapted to delay receipt of said electromagnetic wave of interest reflected from said presence of said first material within said second material by a time period sufficient to distinguish between said reflected electromagnetic wave of interest and a spurious electromagnetic wave reflected from a discontinuity of said second material; and a feeding transition section, wherein said feeding end adapts a radiofrequency signal from and to said electromagnetic wave, and wherein said feeding end is configured to reduce a plurality of reflections of said excited electromagnetic wave at said feeding end, by a sufficient extent so as to reduce a level of clutter otherwise present in said electromagnetic wave launcher; wherein said electromagnetic wave launcher is further physically configured so as to reduce a level of clutter otherwise present in said electromagnetic wave launcher by at least 10 dB; and wherein said housing mounts said electromagnetic wave launcher and said feeding transition section;
   b. determining a type of a low-ringing EM wave launcher to be used for evaluating said status of a region of said first material;
   c. placing said launching end of said EM wave launcher adjacent to said region of said first material;
   d. launching a plurality of EM waves, propagating within a predetermined frequency range, into said region of said first material;
   e. measuring a set of data pertaining to a group of EM waves coming into said EM wave launcher as a result of a propagation of said plurality of EM waves launched by said EM wave launcher; and
   f. determining said status of said first material based upon an identification of said presence of said first material within said second material.

21. The method of claim 20, wherein said type of said low-ringing EM wave launcher is part of a device selected from the group consisting of a fixed device, a portable device, and a handheld device.

22. The method of claim 20, wherein said step of placing said launching end of said EM wave launcher further comprises placing said launching end of said EM wave launcher within two inches of an outer surface of a physical structure adjacent and as close as possible to said region of said first material.

23. The method of claim 20, wherein said status includes a location and an extent of a penetration of said first material within said second material.

24. The method of claim 20, wherein determining said status of said first material further comprises:
   a. transforming said set of data into a domain suitable for further data processing;
   b. processing said set of data by means of at least one data processing method;
   c. calibrating said set of data; and
   d. determining a location and an extent of a penetration of said first material within said second material.

25. The method of claim 20, wherein determining said status of said first material further comprises:
   a. providing a means for storing said set of data;
   b. providing a computer-based data processor for processing said set of data for evaluating said status of said first material;
   c. transferring said set of data from said means for storing said set of data to said computer-based data processor; and
   d. processing said set of data by means of at least one data processing method.

26. The method of claim 20, further comprising the step of processing said set of data utilizing a data processing method selected according to a characteristic of said first material to be evaluated.

27. The method of claim 20, wherein said processing of said set of data determines a thickness of said second material.

28. The method of claim 20, further comprising the step of visually displaying information about said status of said first material.

29. The device of claim 20, wherein said launching end of said electromagnetic wave launcher further comprises at least one smooth edge that follows a shape of a curve through an outer-most portion of said launching end.

30. The device of claim 29, wherein said curve extends from an interior side of said edge through said outer-most part of said launching end and to an exterior side of said edge.

* * * * *